United States Patent

Tillyer et al.

[11] Patent Number: 5,998,625
[45] Date of Patent: Dec. 7, 1999

[54] ASYMMETRIC CONJUGATE ADDITION REACTION USING A CHIRAL ADDITIVE

[75] Inventors: Richard D. Tillyer, Westfield; David M. Tschaen, Holmdel, both of N.J.; Feng Xu, Staten Island, N.Y.

[73] Assignee: Merck & Co., Inc., Rathway, N.J.

[21] Appl. No.: 09/003,050

[22] Filed: Jan. 5, 1998

Related U.S. Application Data

[60] Provisional application No. 60/035,462, Jan. 14, 1997.

[51] Int. Cl.[6] ............... C07D 211/70; C07D 211/72
[52] U.S. Cl. ............... 546/342; 546/339; 546/340; 546/341
[58] Field of Search .................. 546/342, 341, 546/340, 339

[56] References Cited

U.S. PATENT DOCUMENTS 5,389,620  2/1995  Ishikawa et al. ............ 514/80
5,714,479  2/1998  Ishikawa et al. ............ 514/80

FOREIGN PATENT DOCUMENTS

0526708A1  6/1992  European Pat. Off. .
WO93/08799  5/1993  WIPO .

OTHER PUBLICATIONS

Chemical Abstracts 124:175888, abstract of Leonard, Tetrahedron (1995), 51(47), pp. 12843–12858.
chemical Abstracts 122:81251, abstract of Castle, Tetrahedron Lett, (1994), 35(40), pp. 7455–7458.
Chemical Abstracts 117:47646, abstract of Christenson, Tetrahedron, (1992), 48(17), pp. 3623–3632.

*Primary Examiner*—D M Mach
*Attorney, Agent, or Firm*—Valerie J. Camara; Mark R. Daniel

[57] ABSTRACT

This invention relates to a process for the preparation of a key intermediate using an chiral additive to effect an asymmetric conjugate addition.

18 Claims, No Drawings

ASYMMETRIC CONJUGATE ADDITION REACTION USING A CHIRAL ADDITIVE

RELATED APPLICATIONS

This application claims the benefit of U.S. Provisional Application No. 60/035,462 filed Jan. 14, 1997.

BACKGROUND OF THE INVENTION

The present invention relates to novel key intermediates in the synthesis of an endothelin antagonist and the method for preparing these key intermediates of formula I.

The compound possessing a high affinity for at least one of two receptor subtypes, are responsible for the dilation of smooth muscle, such as blood vessels or in the trachea. The endothelin antagonist compounds provide a potentially new therapeutic target, particularly for the treatment of hypertension, pulmonary hypertension, Raynaud's disease, acute renal failure, myocardial infarction, angina pectoris, cerebral infarction, cerebral vasospasm, arteriosclerosis, asthma, gastric ulcer, diabetes, restenosis, prostatauxe endotoxin shock, endotoxin-induced multiple organ failure or disseminated intravascular coagulation, and/or cyclosporin-induced renal failure or hypertension.

Endothelin is a polypeptide composed of amino acids, and it is produced by vascular endothelial cells of human or pig. Endothelin has a potent vasoconstrictor effect and a sustained and potent pressor action (Nature, 332, 411–415 (1988)).

Three endothelin isopeptides (endothelin-1, endothelin-2 and endothelin-3), which resemble one another in structure, exist in the bodies of animals including human, and these peptides have vasoconstriction and pressor effects (Proc. Natl. Acad, Sci, USA, 86, 2863–2867 (1989)).

As reported, the endothelin levels are clearly elevated in the blood of patients with essential hypertension, acute myocardial infarction, pulmonary hypertension, Raynaud's disease, diabetes or atherosclerosis, or in the washing fluids of the respiratory tract or the blood of patients with asthmaticus as compared with normal levels (Japan, J. Hypertension, 12, 79, (1989), J. Vascular medicine Biology, 2, 207 (1990), Diabetologia, 33, 306–310 (1990), J. Am. Med. Association, 264, 2868 (1990), and The Lancet, ii, 747–748 (1989) and ii, 1144–1147 (1990)).

Further, an increased sensitivity of the cerebral blood vessel to endothelin in an experimental model of cerebral vasospasm (Japan. Soc. Cereb. Blood Flow & Metabol., 1, 73 (1989)), an improved renal function by the endothelin antibody in an acute renal failure model (J. Clin, invest., 83, 1762–1767 (1989), and inhibition of gastric ulcer development with an endothelin antibody in a gastric ulcer model (Extract of Japanese Society of Experimental Gastric Ulcer, 50 (1991)) have been reported. Therefore, endothelin is assumed to be one of the mediators causing acute renal failure or cerebral vasospasm following subarachnoid hemorrhage.

Further, endothelin is secreted not only by endothelial cells but also by tracheal epithelial cells or by kidney cells (FEBS Letters, 255, 129–132 (1989), and FEBS Letters, 249, 42–46 (1989)).

Endothelin was also found to control the release of physiologically active endogenous substances such as renin, atrial natriuretic peptide, endothelium-derived relaxing factor (EDRF), thromboxane $A_2$, prostacyclin, noradrenaline, angiotensin II and substance P (Biochem. Biophys, Res. Commun., 157, 1164–1168 (1988); Biochem. Biophys, Res. Commun., 155, 20 167–172 (1989); Proc. Natl. Acad. Sci. USA, 85 1 9797–9800 (1989); J. Cardiovasc. Pharmacol., 13, S89–S92 (1989); Japan. J. Hypertension, 12, 76 (1989) and Neuroscience Letters, 102, 179–184 (1989)). Further, endothelin causes contraction of the smooth muscle of gastrointestinal tract and the uterine smooth muscle (FEBS Letters, 247, 337–340 (1989); Eur. J. Pharmacol., 154, 227–228 (1988); and Biochem. Biophys Res. Commun., 159, 317–323 (1989)). Further, endothelin was found to promote proliferation of rat vascular smooth muscle cells, suggesting a possible relevance to the arterial hypertrophy (Atherosclerosis, 78, 225–228 (1989)). Furthermore, since the endothelin receptors are present in a high density not only in the peripheral tissues but also in the central nervous system, and the cerebral administration of endothelin induces a behavioral change in animals, endothelin is likely to play an important role for controlling nervous functions (Neuroscience Letters, 97, 276–279 (1989)). Particularly, endothelin is suggested to be one of mediators for pain (Life Sciences, 49, PL61–PL65 (1991)).

Internal hyperplastic response was induced by rat carotid artery balloon endothelial denudation. Endothelin causes a significant worsening of the internal hyperplasia (J. Cardiovasc. Pharmacol., 22, 355–359 & 371–373(1993)). These data support a role of endothelin in the phathogenesis of vascular restenosis. Recently, it has been reported that both $ET_A$ and $ET_B$ receptors exist in the human prostate and endothelin produces a potent contraction of it. These results suggest the possibility that endothelin is involved in the pathophysiology of benign prostatic hyperplasia (J. Urology, 151, 763–766(1994), Molecular Pharmocol., 45, 306–311 (1994)).

On the other hand, endotoxin is one of potential candidates to promote the release of endothelin. Remarkable elevation of the endothelin levels in the blood or in the culture supernatant of endothelial cells was observed when endotoxin was exogenously administered to animals or added to the culture endothelial cells, respectively. These findings suggest that endothelin is an important mediator for endotoxin-induced diseases (Biochem. Biophys. Commun., 161, 1220–1227 (1989); and Acta Physiol. Scand., 137, 317–318 (1989)).

Further, it was reported that cyclosporin remarkably increased endothelin secretion in the renal cell culture (LLC-PKL cells) (Eur. J. Pharmacol., 180, 191–192 (1990)). Further, dosing of cyclosporin to rats reduced the glomerular filtration rate and increased the blood pressure in association with a remarkable increase in the circulating endothelin level. This cyclosporin-inducea renal failure can be suppressed by the administration of endothelin antibody (Kidney Int., 37, 1487–1491 (1990)). Thus, it is assumed that endothelin is significantly involved in the pathogenesis of the cyclosporin-induced diseases.

Such various effects of endothelin are caused by the binding of endothelin to endothelin receptors widely distributed in many tissues (Am. J. Physiol., 256, R856–R866 (1989)).

It is known that vasoconstriction by the endothelins is caused via at least two subtypes of endothelin receptors (J. Cardiovasc. Pharmacol., 17(Suppl.7), S119–SI21 (1991)). One of the endothelin receptors is $ET_A$ receptor Selective to ET-1 rather than ET-3, and the other is $ET_B$ receptor equally active to ET-1 and ET-3. These receptor proteins are reported to be different from each other (Nature, 348, 730–735 (1990)).

These two subtypes of endothelin receptors are differently distributed in tissues. It is known that the $ET_A$ receptor is present mainly in cardiovascular tissues, whereas the $ET_B$ receptor is widely distributed in various tissues such as brain, kidney, lung, heart and vascular tissues.

Substances which specifically inhibit the binding of endothelin to the endothelin receptors are believed to antagonize various pharmacological activities of endothelin and to be useful as a drug in a wide field. Since the action of the endothelins is caused via not only the $ET_A$ receptor but also the $ET_B$ receptor, novel non-peptidic substances with ET receptor antagonistic activity to either receptor subtype are desired to block activities of the endothelins effectively in various diseases.

Endothelin is an endogenous substance which directly or indirectly (by controlling liberation of various endogenous substances) induces sustained contraction or relaxation of vascular or non-vascular smooth muscles, and its excess production or excess secretion is believed to be one of pathogeneses for hypertension, pulmonary hypertension, Raynaud's disease, bronchial asthma, gastric ulcer, diabetes, arteriosclerosis, restenosis, acute renal failure, myocardial infarction, angina pectoris, cerebral vasospasm and cerebral infarction. Further, it is suggested that endothelin serves as an important mediator involved in diseases such as restenosis, prostatauxe, endotoxin shock, endotoxin-induced multiple organ failure or disseminated intravascular coagulation, and cyclosporin-induced renal failure or hypertension.

Two endothelin receptors $ET_A$ and $ET_B$ are known so far and antagonists of these receptors have been shown to be potential drug induced targets. EP 0526708 A1 and WO 93/08799 A1 are representative examples of patent applications disclosing non-peptidic compounds with alleged activity as endothelin receptor antagonists.

The present invention discloses an asymmetric conjugate addition for preparing the compound of Formula I,

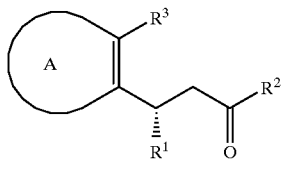

a key intermediate in the synthesis of endothelin antagonists of the following structure:

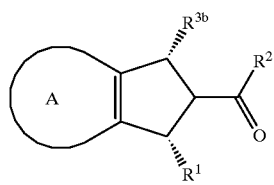

wherein

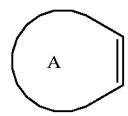

represents: 5- or 6-membered heterocyclyl, 5- or 6-membered carbocyclyl, and aryl;

$R^1$ is: $C_1$–$C_8$ alkyl, $C_2$–$C_8$ alkenyl, $C_2$–$C_8$ alkynyl, $C_3$–$C_8$ cycloalkyl, aryl, or heteroaryl;

$R^2$ is $OR^4$ and $N(R^5)_2$;

$R^{3b}$ is aryl, or heteroaryl;

$R^4$ is $C_1$–$C_8$ alkyl; and $R^5$ is: $C_1$–$C_8$ alkyl, or aryl.

SUMMARY OF THE INVENTION

The instant invention relates to a process for the preparation of a compound of formula I:

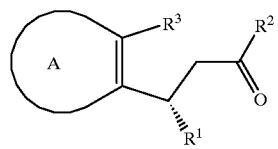

wherein

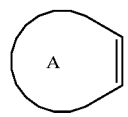

represents:

a) 5- or 6-membered heterocyclyl containing one, two or three double bonds, but at least one double bond and 1, 2 or 3 heteroatoms selected from O, N and S, the heterocyclyl is unsubstituted or substituted with one, two or three substituents selected from the group consisting of: OH, $CO_2R^4$, Br, Cl, F, I, $CF_3$, $N(R^5)_2$, $C_1$–$C_8$ alkoxy, $C_1$–$C_8$ alkyl, $C_2$–$C_8$ alkenyl, $C_2$–$C_8$ alkynyl, or $C_3$–$C_8$ cycloalkyl, $CO(CH_2)_nCH_3$, and $CO(CH_2)_nCH_2N(R^5)_2$, b) 5- or 6-membered carbocyclyl containing one or two double bonds, but at least one double bond, the carbocyclyl is unsubstituted or substituted with one, two or three substituents selected from the group consisting of: OH, $CO_2R^4$, Br, Cl, F, I, $CF_3$, $N(R^5)_2$, $C_1$–$C_8$ alkoxy, $C_1$–$C_8$ alkyl, $C_2$–$C_8$ alkenyl, $C_2$–$C_8$ alkynyl, or $C_3$–$C_8$ cycloalkyl, $CO(CH_2)_nCH_3$, and $CO(CH_2)_nCH_2N(R^5)_2$, c) aryl, wherein aryl is as defined below, $C_1$–$C_8$ alkoxy, $C_1$–$C_8$ alkyl, $C_2$–$C_8$ alkenyl, $C_2$–$C_8$ alkynyl, or $C_3$–$C_8$ cycloalkyl, are unsubstituted or substituted with one, two or three substituents selected from the group consisting of: OH, $CO_2R^4$, Br, Cl, F, I, $CF_3$, $N(R^5)_2$, $C_1$–$C_8$ alkoxy, $C_3$–$C_8$ cycloalkyl, $CO(CH_2)_nCH_3$, and $CO(CH_2)_nCH_2N(R^5)_2$, aryl is defined as phenyl or naphthyl, which is unsubstituted or substituted with one, two or three substituents selected from the group consisting of: OH, $CO_2R^4$, Br, Cl, F, I, $CF_3$, $N(R^5)_2$, $C_1$–$C_8$ alkoxy, $C_1$–$C_8$ alkyl, $C_2$–$C_8$ alkenyl, $C_2$–$C_8$ alkynyl, or $C_3$–$C_8$ cycloalkyl, $CO(CH_2)_nCH_3$, $CO(CH_2)_nCH_2N(R^5)_2$, and when two substituents are located on adjacent carbons they can join to form a 5- or 6-membered ring with one, two or three heteroatoms selected from O, N, and S, which is unsubstituted or substituted with with one, two or three substituents selected from the group consisting of: H, OH, $CO_2R^6$, Br, Cl, F, I, $CF_3$, $N(R^7)_2$, $C_1$–$C_8$ alkoxy, $C_1$–$C_8$ alkyl, $C_2$–$C_8$ alkenyl, $C_2$–$C_8$ alkynyl, or $C_3$–$C_8$ cycloalkyl, $CO(CH_2)_nCH_3$, and $CO(CH_2)_nCH_2N(R^5)_2$, $R^1$ is:
a) $C_1$–$C_8$ alkyl, $C_2$–$C_8$ alkenyl, $C_2$–$C_8$ alkynyl, $C_3$–$C_8$ cycloalkyl,
b) aryl, or
c) heteroaryl;
heteroaryl is defined as a 5- or 6-membered aromatic ring containing 1, 2 or 3 heteroatoms selected from O, N and S which is unsubstituted or substituted with one, two or three substituents selected from the group consisting of: OH, $CO_2R^4$, Br, Cl, F, I, $CF_3$, $N(R^5)_2$, $C_1$–$C_8$ alkoxy, $C_1$–$C_8$ alkyl, $C_2$–$C_8$ alkenyl, $C_2$–$C_8$ alkynyl, or $C_3$–$C_8$ cycloalkyl, $CO(CH_2)_nCH_3$, and $CO(CH_2)_nCH_2N(R^5)_2$, $R^2$ is: $OR^4$ or $N(R^5)_2$;

$R^3$ is:
a) H,
b) $C_1$–$C_8$ alkyl,
c) $C_1$–$C_8$ alkenyl,
d) $C_1$–$C_8$ alkynyl,
e) $C_1$–$C_8$ alkoxyl,
f) $C_3$–$C_7$ cycloalkyl,
g) $S(O)_tR^5$,
h) Br, Cl, F, I,
i) aryl,
j) heteroaryl,
k) $N(R^5)_2$,
l) $NH_2$,
m) CHO,
n) —CO—$C_1$–$C_8$ alkyl,
o) —CO-aryl,
p) —CO-heteroaryl,
q) —$CO_2R^4$, or
r) protected aldehyde;

X and Y are independently: O, S, or $NR^5$;
n is: 0 to 5;
t is: 0, 1 or 2;
$R^4$ is: $C_1$–$C_8$ alkyl;
$R^5$ is: $C_1$–$C_8$ alkyl, or aryl;
$R^6$, is: H, $C_1$–$C_8$ alkyl, or aryl;
$R^7$ is: H, $C_1$–$C_8$ alkyl, aryl, which is unsubstituted or substituted with one, two or three substituents selected from the group consisting of: OH, $CO_2R^4$, Br, Cl, F, I, $CF_3$, $N(R^5)_2$, $C_1$–$C_8$ alkoxy, $C_1$–$C_8$ alkyl, $C_2$–$C_8$ alkenyl, $C_2$–$C_8$ alkynyl, or $C_3$–$C_8$ cycloalkyl, $CO(CH_2)_nCH_3$, $CO(CH_2)_nCH_2N(R^5)_2$; or when two $R^7$ substituents are on the same nitrogen they can join to form a ring of 3 to 6 atom;

comprising reacting a α,β-unsaturated ester or amide

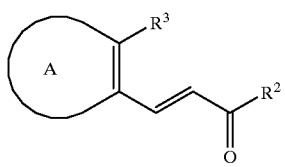

with an organolithium compound, $R^1Li$, in the presence of a chiral additive and an aprotic solvent at a temperature range of about −78° C. to about 0° C.

DETAILED DESCRIPTION OF THE INVENTION

The instant invention relates to a process for the preparation of a compound of formula I:

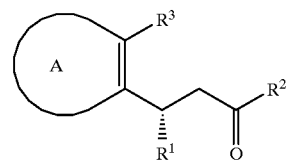

wherein

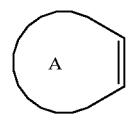

represents:
a) 5- or 6-membered heterocyclyl containing one, two or three double bonds, but at least one double bond and 1, 2 or 3 heteroatoms selected from O, N and S, the heterocyclyl is unsubstituted or substituted with one, two or three substituents selected from the group consisting of: OH, $CO_2R^4$, Br, Cl, F, I, $CF_3$, $N(R^5)_2$, $C_1$–$C_8$ alkoxy, $C_1$–$C_8$ alkyl, $C_2$–$C_8$ alkenyl, $C_2$–$C_8$ alkynyl, or $C_3$–$C_8$ cycloalkyl, $CO(CH_2)_nCH_3$, and $CO(CH_2)_nCH_2N(R^5)_2$, b) 5- or 6-membered carbocyclyl containing one or two double bonds, but at least one double bond, the carbocyclyl is unsubstituted or substituted with one, two or three substituents selected from the group consisting of: OH, $CO_2R^4$, Br, Cl, F, I, $CF_3$, $N(R^5)_2$, $C_1$–$C_8$ alkoxy, $C_1$–$C_8$ alkyl, $C_2$–$C_8$ alkenyl, $C_2$–$C_8$ alkynyl, or $C_3$–$C_8$ cycloalkyl, $CO(CH_2)_nCH_3$, and $CO(CH_2)_nCH_2N(R^5)_2$, c) aryl, wherein aryl is as defined below,
$C_1$–$C_8$ alkoxy, $C_1$–$C_8$ alkyl, $C_2$–$C_8$ alkenyl, $C_2$–$C_8$ alkynyl, or $C_3$–$C_8$ cycloalkyl, are unsubstituted or substituted with one, two or three substituents selected from the group consisting of: OH, $CO_2R^4$, Br, Cl, F, I, $CF_3$, $N(R^5)_2$, $C_1$–$C_8$ alkoxy, $C_3$–$C_8$ cycloalkyl, $CO(CH_2)_nCH_3$, and $CO(CH_2)_nCH_2N(R^5)_2$, aryl is defined as phenyl or naphthyl, which is unsubstituted or substituted with one, two or three substituents selected from the group consisting of: OH, $CO_2R^4$, Br, Cl, F, I, $CF_3$, $N(R^5)_2$, $C_1$–$C_8$ alkoxy, $C_1$–$C_8$ alkyl, $C_2$–$C_8$ alkenyl, $C_2$–$C_8$ alkynyl, or $C_3$–$C_8$ cycloalkyl, $CO(CH_2)_nCH_3$, $CO(CH_2)_nCH_2N(R^5)_2$, and when two substituents are located on adjacent carbons they can join to form a 5- or 6-membered ring with one, two or three heteroatoms selected from O, N, and S, which is unsubstituted or substituted with one, two or three substituents selected from the group consisting of: H, OH, $CO_2R^6$, Br, Cl, F, I, $CF_3$, $N(R^7)_2$, $C_1$–$C_8$ alkoxy, $C_1$–$C_8$ alkyl, $C_2$–$C_8$ alkenyl, $C_2$–$C_8$ alkynyl, or $C_3$–$C_8$ cycloalkyl, $CO(CH_2)_nCH_3$, and $CO(CH_2)_nCH_2N(R^5)_2$, $R^1$ is:
a) $C_1$–$C_8$ alkyl, $C_2$–$C_8$ alkenyl, $C_2$–$C_8$ alkynyl, $C_3$–$C_8$ cycloalkyl,
b) aryl, or
c) heteroaryl;

heteroaryl is defined as a 5- or 6-membered aromatic ring containing 1, 2 or 3 heteroatoms selected from O, N and S, which is unsubstituted or substituted with one, two or three substituents selected from the group consisting of: OH, $CO_2R^4$, Br, Cl, F, I, $CF_3$, $N(R^5)_2$, $C_1$–$C_8$ alkoxy, $C_1$–$C_8$ alkyl, $C_2$–$C_8$ alkenyl, $C_2$–$C_8$ alkynyl, or $C_3$–$C_8$ cycloalkyl, $CO(CH_2)_nCH_3$, and $CO(CH_2)_nCH_2N(R^5)_2$, $R^2$ is $OR^4$ or $N(R^5)_2$;

$R^3$ is a) H, b) $C_1$–$C_8$ alkyl, c) $C_1$–$C_8$ alkenyl, d) $C_1$–$C_8$ alkynyl, e) $C_1$–$C_8$ alkoxyl, f) $C_3$–$C_7$ cycloalkyl, g) $S(O)_tR^5$, h) Br, Cl, F, I, i) aryl, j) heteroaryl, k) $N(R^5)_2$, l) $NH_2$, m) CHO, n) —CO—$C_1$–$C_8$ alkyl, o) —CO-aryl, p) —CO-heteroaryl, q) —$CO_2R^4$, or r) protected aldehyde;

X and Y are independently: O, S, or $NR^5$;

n is: 0 to 5;

t is: 0, 1 or 2;

$R^4$ is $C_1$–$C_8$ alkyl;

$R^5$ is: $C_1$–$C_8$ alkyl, or aryl; and $R^6$ is: H, $C_1$–$C_8$ alkyl, and aryl; and $R^7$ are independently: H, $C_1$–$C_8$ alkyl, and aryl, when there are two $R^7$ substituents on a nitrogen they can join to form a 3- through 6-membered ring, which is unsubstituted or substituted with one, two or three substituents selected from the group consisting of: OH, $CO_2R^4$, Br, Cl, F, I, $CF_3$, $N(R^5)_2$, $C_1$–$C_8$ alkoxy, $C_1$–$C_8$ alkyl, $C_2$–$C_8$ alkenyl, $C_2$–$C_8$ alkynyl, or $C_3$–$C_8$ cycloalkyl, $CO(CH_2)_nCH_3$, $CO(CH_2)_nCH_2N(R^5)_2$;

comprising reacting a α,β-unsaturated ester or amide

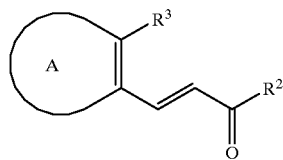

with an organolithium compound, $R^1Li$, in the presence of a chiral additive and an aprotic solvent at a temperature range of about −78° C. to about 0° C.

The process as recited above, wherein the number of equivalents of the organolithium compound, $R^1Li$, is 1 to about 4, and preferably about 1.5 to about 2.5.

The process as recited above, wherein the chiral additive is a chiral compound capable of coordinating with the α,β-unsaturated ester or amide and organolithium, such as a) (−)-sparteine, b) N,N,N',N'-tetra($C_1$–$C_6$)-alkyltrans-1,2-diaminocyclohexane, or c)

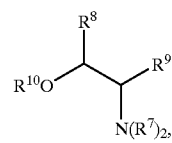

wherein $R^8$ and $R^9$ are independently: H, $C_1$–$C_6$ alkyl, $C_3$–$C_7$ cycloalkyl or aryl, except that $R^8$ and $R^9$ cannot simultaneously be H; and $R^{10}$ is $C_1$–$C_6$ alkyl or aryl, are useful in this process. It is understood that the amino alcohol represented by the above noted structure has at least one, and potentially two chiral centers.

The process as recited above, wherein the aprotic solvent is selected from the group consisting of tetrahydrofuran, diethyl ether, MTBE (methyl t-butyl ether), toluene, benzene, hexane, pentane, and dioxane, or a mixture of said solvents. The process as recited above, wherein the preferred aprotic solvent is toluene.

The solvent mixtures useful in this process are: hexane and toluene with a catalytic amount of tetrahydrofuran, and pentane and toluene with a catalytic amount of tetrahydrofuran, preferrably hexane and toluene with a catalytic amount of tetrahydrofuran.

The process as recited above, wherein the temperature range is about −78° C. to about −20° C., and preferably about −78° C. to about −50° C.

An embodiment of this invention is the process for the preparation of a compound of formula I:

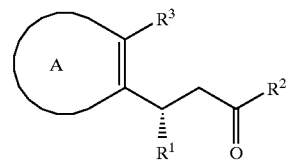

wherein

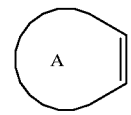

represents:

a) 5- or 6-membered heterocyclyl containing one, two or three double bonds, but at least one double bond and 1, 2 or 3 heteroatoms selected from O, N and S, the heterocyclyl is unsubstituted or substituted with one, two or three substituents selected from the group consisting of: OH, $CO_2R^4$, Br, Cl, F, I, $CF_3$, $N(R^5)_2$, $C_1$–$C_8$ alkoxy, $C_1$–$C_8$ alkyl, $C_2$–$C_8$ alkenyl, $C_2$–$C_8$ alkynyl, or $C_3$–$C_8$ cycloalkyl, $CO(CH_2)_nCH_3$, and $CO(CH_2)_nCH_2N(R^5)_2$, b) 5- or 6-membered carbocyclyl containing one or two double bonds, but at least one double bond, the carbocyclyl is unsubstituted or substituted with one, two or three substituents selected from the group consisting of: OH, $CO_2R^4$, Br, Cl, F, I, $CF_3$, $N(R^5)_2$, $C_1$–$C_8$ alkoxy, $C_1$–$C_8$ alkyl, $C_2$–$C_8$ alkenyl, $C_2$–$C_8$ alkynyl, or $C_3$–$C_8$ cycloalkyl, $CO(CH_2)_nCH_3$, and $CO(CH_2)_nCH_2N(R^5)_2$, c) aryl, wherein aryl is as defined below, $C_1$–$C_8$ alkoxy, $C_1$–$C_8$ alkyl, $C_2$–$C_8$ alkenyl, $C_2$–$C_8$ alkynyl, or $C_3$–$C_8$ cycloalkyl, are unsubstituted or substituted with one, two or three substituents selected from the group consisting of: OH, $CO_2R^4$, Br, Cl, F, I, $CF_3$, $N(R^5)_2$, $C_1$–$C_8$ alkoxy, $C_3$–$C_8$ cycloalkyl, $CO(CH_2)_nCH_3$, and $CO(CH_2)_nCH_2N(R^5)_2$, aryl is defined as phenyl or naphthyl, which is unsubstituted or substituted with one, two or three substituents selected from the group consisting of: OH, $CO_2R^4$, Br, Cl, F, I, $CF_3$, $N(R^5)_2$, $C_1$–$C_8$ alkoxy, $C_1$–$C_8$ alkyl, $C_2$–$C_8$ alkenyl, $C_2$–$C_8$ alkynyl, or $C_3$–$C_8$ cycloalkyl, $CO(CH_2)_nCH_3$, $CO(CH_2)_nCH_2N(R^5)_2$, and when two substituents are located on adjacent carbons they can join to form a 5- or 6-membered ring with one, two or three heteroatoms selected from O, N, and S, which is unsubstituted or substituted with one, two or three substituents selected from the group consisting of: H, OH, $CO_2R^6$, Br, Cl, F, I, $CF_3$, $N(R^7)_2$, $C_1$–$C_8$ alkoxy, $C_1$–$C_8$ alkyl, $C_2$–$C_8$ alkenyl, $C_2$–$C_8$ alkynyl, or $C_3$–$C_8$ cycloalkyl, $CO(CH_2)_nCH_3$, and $CO(CH_2)_nCH_2N(R^5)_2$, $R^1$ is:

a) $C_1$–$C_8$ alkyl, $C_2$–$C_8$ alkenyl, $C_2$–$C_8$ alkynyl, $C_3$–$C_8$ cycloalkyl, b) aryl, or c) heteroaryl;

heteroaryl is defined as a 5- or 6-membered aromatic ring containing 1, 2 or 3 heteroatoms selected from O, N and S, which is unsubstituted or substituted with one, two or three substituents selected from the group consisting of: OH, $CO_2R^4$, Br, Cl, F, I, $CF_3$, $N(R^5)_2$, $C_1$–$C_8$ alkoxy, $C_1$–$C_8$ alkyl, $C_2$–$C_8$ alkenyl, $C_2$–$C_8$ alkynyl, or $C_3$–$C_8$ cycloalkyl, $CO(CH_2)_nCH_3$, and $CO(CH_2)_nCH_2N(R^5)_2$, $R^2$ is $OR^4$ or $N(R^5)_2$;

$R_3$ is a) CHO, b) $CH(OR^4)_2$;

n is: 0 to 5, t is: 0, 1 or 2;

X and Y are independently: O, S, or $NR^5$;

$R^4$ is $C_1$–$C_8$ alkyl;

$R^5$ is: $C_1$–$C_8$ alkyl, or aryl;

$R^6$ is: H, $C_1$–$C_8$ alkyl, and aryl;

$R^7$ are independently: H, $C_1$–$C_8$ alkyl, and aryl, when there are two $R^7$ substituents on a nitrogen they can join to form a 3- through 6-membered ring, which is unsubstituted or substituted with one, two or three substituents selected from the group consisting of: OH, $CO_2R^4$, Br, Cl, F, I, $CF_3$, $N(R^5)_2$, $C_1$–$C_8$ alkoxy, $C_1$–$C_8$ alkyl, $C_2$–$C_8$ alkenyl, $C_2$–$C_8$ alkynyl, or $C_3$–$C_8$ cycloalkyl, $CO(CH_2)_nCH_3$, $CO(CH_2)_nCH_2N(R^5)_2$;

comprising the steps of:

1) reacting an α,β-unsaturated ester or amide

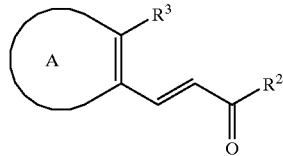

where $R^3$ is $CH(OR^4)_2$;

with an organolithium compound, $R^1Li$, in the presence of a chiral additive and an aprotic solvent at a temperature range of about −78° C. to about 0° C. to give the conjugate adduct; and 2) removing the aldehyde protecting group with an acid to give the compound of Formula I, where $R^3$ is CHO.

The process as recited above, wherein the number of equivalents of the organolithium compound, $R^1Li$, is 1 to about 4, and preferably about 1.5 to about 2.5.

The process as recited above, wherein the chiral additive is a chiral compound capable of coordinating with the α,β-unsaturated ester or amide and organolithium, such as a) (−)-sparteine, b) N,N,N',N'-tetra($C_1$–$C_6$)-alkyltrans-1,2-diaminocyclohexane, or c)

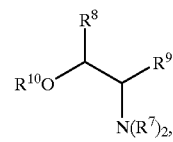

wherein $R^8$ and $R^9$ are independently: H, $C_1$–$C_6$ alkyl, $C_3$–$C_7$ cycloalkyl or aryl, except that $R_8$ and $R^9$ cannot simultaneously be H; and $R^{10}$ is $C_1$–$C_6$ alkyl or aryl, are useful in this process.

The process as recited above, wherein the aprotic solvent is selected from the group consisting of tetrahydrofuran, diethyl ether, MTBE (methyl t-butyl ether), toluene, benzene, hexane, pentane, and dioxane, or a mixture of said solvents. The process as recited above, wherein the preferred aprotic solvent is toluene.

The solvent mixtures useful in this process are: hexane and toluene with a catalytic amount of tetrahydrofuran, and pentane and toluene with a catalytic amount of tetrahydrofuran, preferrably hexane and toluene with a catalytic amount of tetrahydrofuran.

The solvent mixtures useful in this process are: hexane and toluene with a catalytic amount of tetrahydrofuran, and pentane and toluene with a catalytic amount of tetrahydrofuran, preferrably hexane and toluene with a catalytic amount of tetrahydrofuran.

The process as recited above, wherein the temperature range is about −78° C. to about −20° C., and preferably about −78° C. to about −50° C.

An embodiment of this invention is the process for the preparation of the protected aldehyde

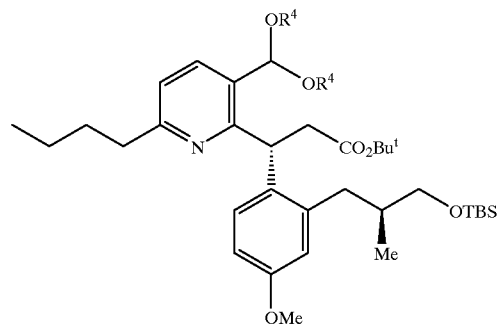

comprising reacting an α,β-unsaturated ester or amide

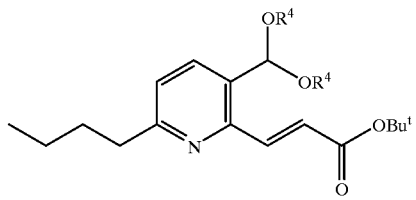

with an organolithium compound

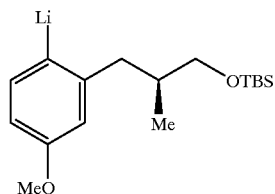

in the presence of a chiral additive and an aprotic solvent at a temperature range of about −78° C. to about −20° C.

The process as recited above, wherein the number of equivalents of the organolithium compound, $R^1Li$, is 1 to about 4, and preferably about 1.5 to about 2.5.

The process as recited above, wherein the chiral additive is a chiral compound capable of coordinating with the α,β-unsaturated ester or amide and organolithium, such as
 a) (−)-sparteine,
 b) N,N,N',N'-tetra($C_1$–$C_6$)-alkyltrans-1,2-diaminocyclohexane, or
 c)

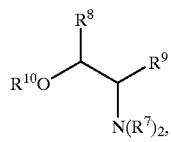

wherein $R^8$ and $R^9$ are independently: H, $C_1$–$C_6$ alkyl, $C_3$–$C_7$ cycloalkyl or aryl, except that $R^8$ and $R^9$ cannot simultaneously be H; and $R^{10}$ is $C_1$–$C_6$ alkyl or aryl, are useful in this process.

The process as recited above, wherein the aprotic solvent is selected from the group consisting of tetrahydrofuran, diethyl ether, MTBE (methyl t-butyl ether), toluene, benzene, hexane, pentane, and dioxane, or a mixture of said solvents. The process as recited above, wherein the preferred aprotic solvent is tetrahydorfuran.

The solvent mixtures useful in this process are: hexane and toluene with a catalytic amount of tetrahydrofuran, and pentane and toluene with a catalytic amount of tetrahydrofuran, preferrably hexane and toluene with a catalytic amount of tetrahydrofuran.

The process as recited above, wherein the temperature range is about −78° C. to about −20° C., preferably about −78° C. to about −50° C., and most preferably about −78° C. to about −70° C.

It is further understood that the substituents recited above would include the definitions recited below.

The alkyl substituents recited above denote straight and branched chain hydrocarbons of the length specified such as methyl, ethyl, isopropyl, isobutyl, tert-butyl (herein referred to as Bu), neopentyl, isopentyl, etc.

The alkenyl-substituents denote alkyl groups as described above which are modified so that each contains a carbon to carbon double bond such as vinyl, allyl and 2-butenyl.

Cycloalkyl denotes rings composed of 3 to 8 methylene groups, each of which may be substituted or unsubstituted with other hydrocarbon substituents, and include for example cyclopropyl, cyclopentyl, cyclohexyl and 4-methylcyclohexyl.

The alkoxy substituent represents an alkyl group as described above attached through an oxygen bridge.

The heteroaryl substituent represents an carbazolyl, furanyl, thienyl, pyrrolyl, isothiazolyl, imidazolyl, isoxazolyl, thiazolyl, oxazolyl, pyrazolyl, pyrazinyl, pyridyl, pyrimidyl, purinyl.

The heterocyclyl substituent represents a pyridyl, pyrimidyl, thienyl, furanyl, oxazolidinyl, oxazolyl, thiazolyl, isothiazolyl, pyrazolyl, triazolyl, imidazolyl, imidazoldinyl, thiazolidilnyl, isoxazolyl, oxadiazolyl, thiadiazolyl, morpholinyl, piperidinyl, piperazinyl, pyrrolyl, or pyrrolidinyl.

The protected aldehyde represents an acetal, such as —CH(O$C_1$–$C_8$ alkyl)$_2$,

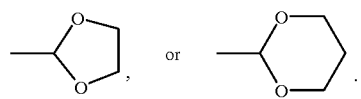

The α,β-unsaturated ester or amide

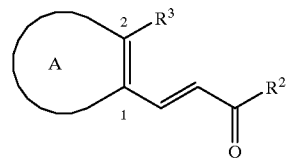

can generally be prepared in two steps:

1) a coupling reaction at the one position of Ring A

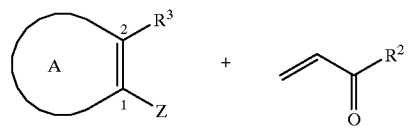

wherein $R^3$ is CHO, Z is a leaving group, such as Br, Cl, I, OTriflyl, OTosyl or OMesyl and $R^2$ is $OR^4$ or $N(R^5)_2$; and 2) the conversion of the aldehyde ($R^3$ is CHO) to the desired protected aldehyde ($R^3$ is $CH(OR^4)_2$ and $R^4$ is $C_1$–$C_8$ alkyl).

Commercially available pyridone 1 is alkylated via its dianion with propyl bromide, and the product is then converted into the bromopyridine 3a using a brominating agent such as $PBr_3$. The nitrile 3a is then reduced to the aldehyde 3 using diisobutyl aluminum hydride (DIBAL). The aldehyde then undergoes a Heck reaction with t-butyl acrylate using NaOAc, (allyl)$_2$PdCl$_2$, tri-o-tolylphosphine, toluene, reflux to provide the unsaturated ester 4a in high yield. The unsaturated ester 4a is then treated with an alcohol ($R^4$OH) and aqueous acid to give the acetal-acceptor 5a.

Scheme 1

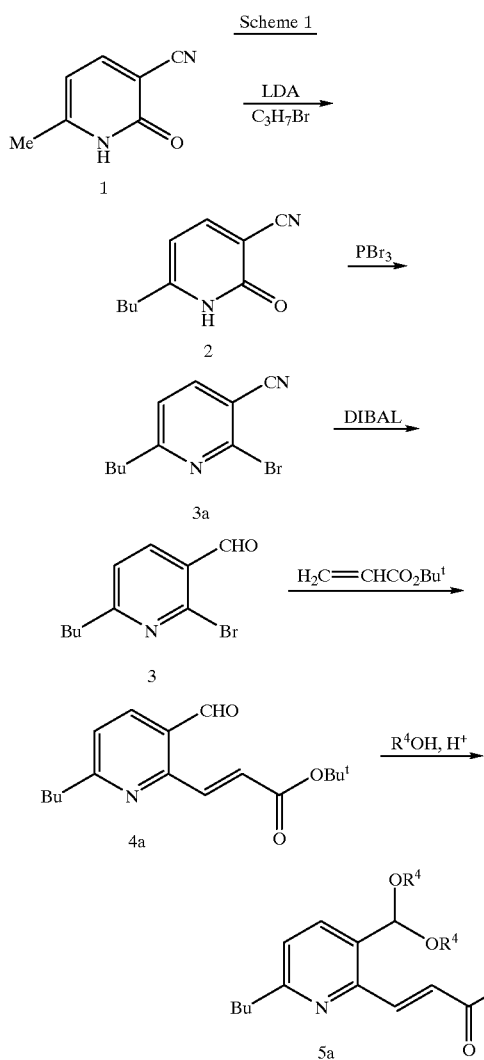

Commericially available acid 10 is reduced with $BH_3 \cdot SMe_2$, to the alcohol 11, which is then converted into the bromide 13, via the mesylate 12 using mesyl chloride, triethylamine followed by the addition of NaBr and dimethylacetamide (DMAC).

Scheme 2

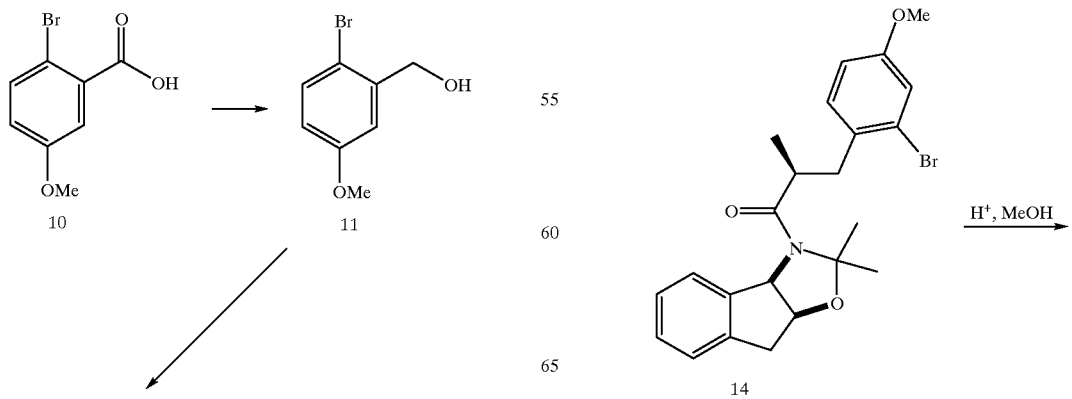

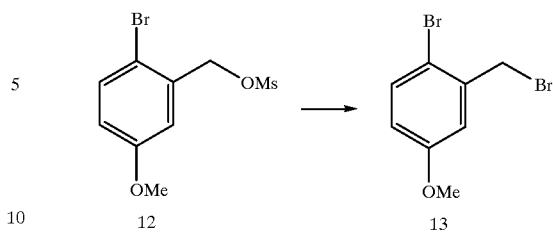

Commercial available 1,2-amino indanol is acylated (propionyl choride, $K_2CO_3$) to give amide 8, which is then converted into the acetonide 9 (2-methoxypropene, pyridinium p-toluene-sulfonate (PPTS)). Acetonide 9 is then alkylated with the bromide 13, (LiHMDS) to give 14, which is then hydrolyzed (H+, MeOH) to give a mixture of acid and methyl ester 15. Reduction (LAH) of the ester/acid mixture provided the alcohol 16 in high yield and optical purity. Protection of the alcohol 16 (TBSCl, imidazole) provided bromide 17, the precursor to organolithium 17a.

Scheme 3

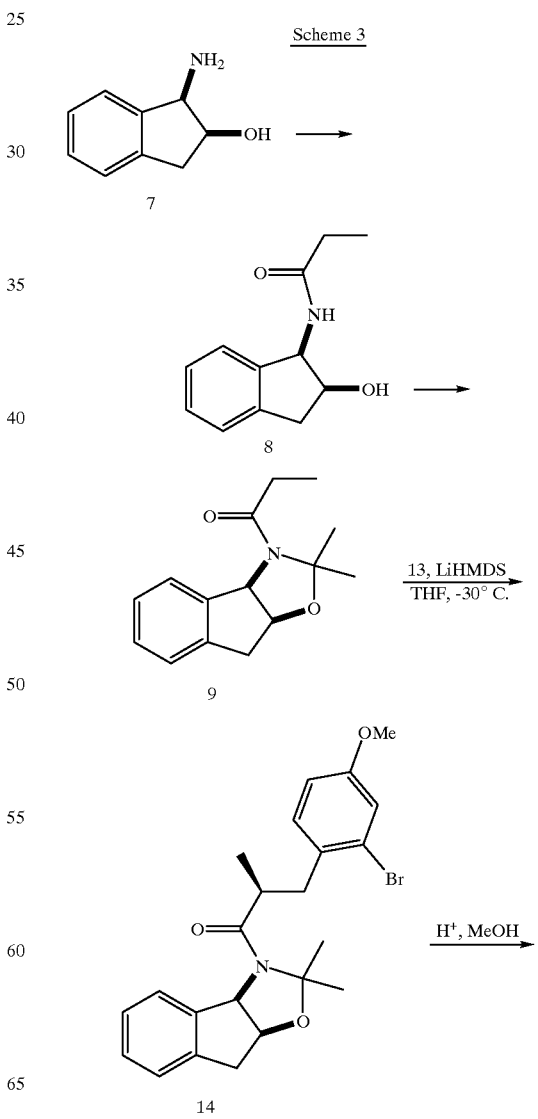

15
-continued
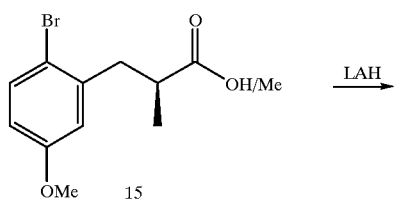
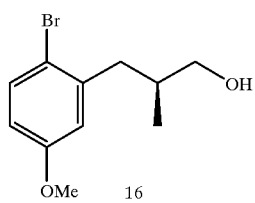
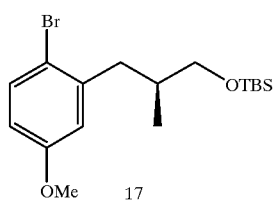
16
-continued
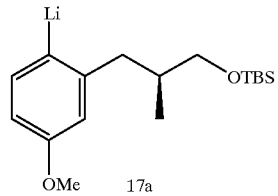
Compound 17a and a chiral additive, such as sparteine, are added to the α,β-unsaturated ester 5a at −78° C. to −50° C. Work up with water affords compounds 6a and 6b. Mixtures of compounds 6a and 6b are treated with TBAF or aqueous acid to deprotect the silylated alcohol or acetal and silylated alcohol.
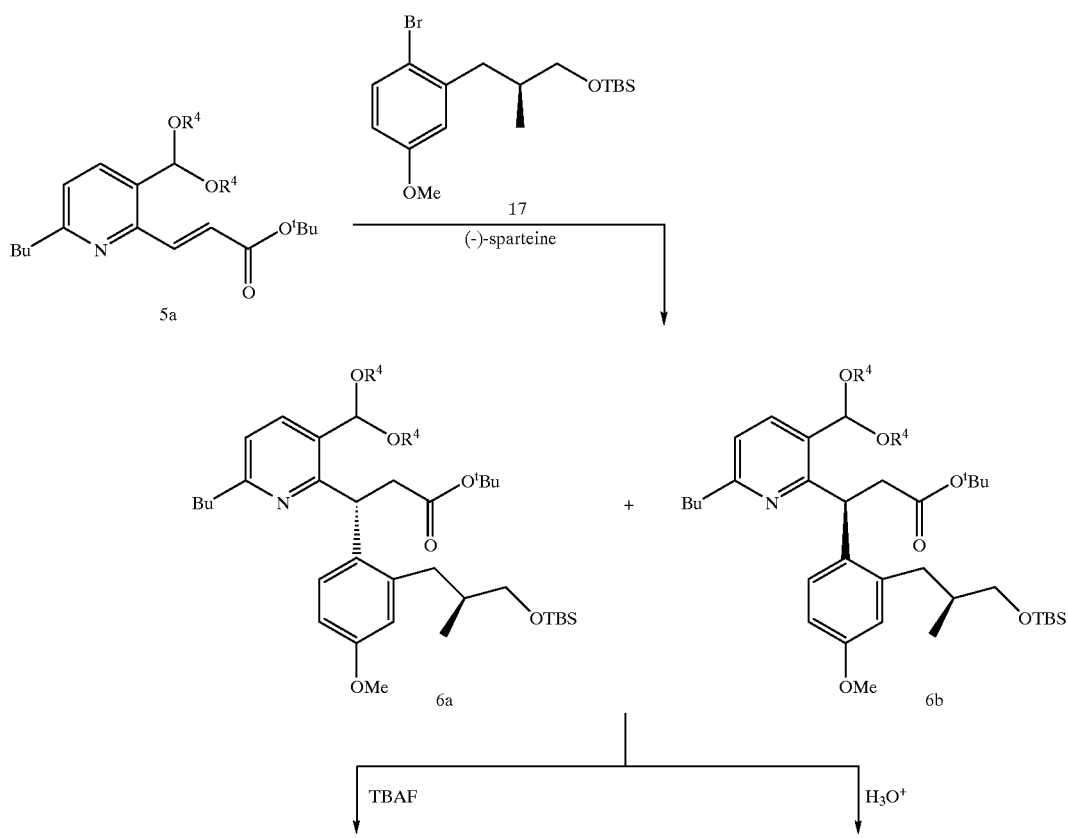

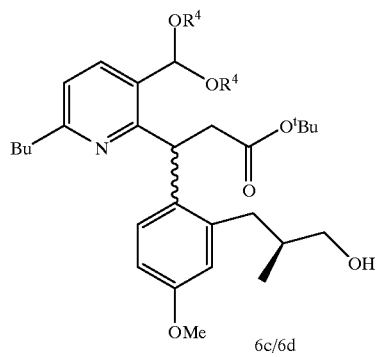

6c/6d

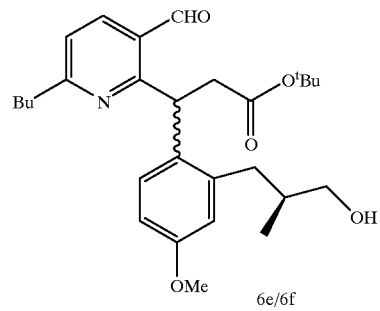

6e/6f

The instant invention can be understood further by the following examples, which do not constitute a limitation of the invention.

EXAMPLE 1

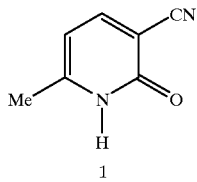

1

Preparation of 1

Compound 1 is a commericially available starting material, for example, see Aldrich Chemical Company, Milwaukee, Wis., USA 53201.

EXAMPLE 2

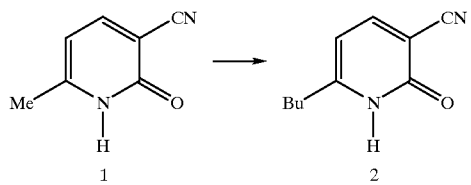

Preparation of 2

Diisopropyl amine (MW 101.19, d 0.772, 2.1 equ, 20.54 mL) in 200 mL THF. Cool to −50° C. and add n-BuLi (1.6 M in hexanes, 2.05 equ, 96 mL), allowing solution to warm to −20° C. Age 0–3° C. for 15 min, then cool to −30° C. and add 1 (MW 134.14, 75 mmol, 10.0 g). Age 0° C. to 43° C. for 2 h. Cool to −50° C. and add bromopropane (MW 123.00, d 1.354, 1.0 equ, 6.8 mL). Warm to 25° C. over 30 min, and age 30 min. Add $NH_4Cl$ and $CH_2Cl_2$. Dry organic (magnesium sulfate) then evaporate in vacuo to afford 61% of 2.

EXAMPLE 3

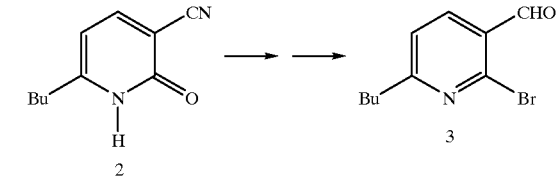

Preparation of 3

Mix 2 (MW 176.22, 46 mmol) and $PBr_3$ (MW 270.70, d 2.880, 2.5 equ, 10.8 mL) and age at 160° C. After 2 h, cool to 25° C. and add some $CH_2Cl_2$. Slowly quench by adding water. Separate layers and wash aqueous two times with $CH_2Cl_2$. Combine organic layers and dry (magnesium sulfate). Concentrate and isolate solid by silica gel chromatography (90:10 hexanes:ethyl acetate) in 60% yield (MW 239.12, 6.60 g).

Dissolve product of bromination reaction (MW 239.12, 27.6 mmol, 6.60 g) in 66 mL toluene and cool to −42° C. Slowly add DIBAL (1.5 M in toluene, 2 equ, 37 mL) and age 1 h at −42° C. Add HCl (2 N, 10 equ, 134 mL) and stir vigorously for 30 min. Dilute with ethyl acetate, separate layers, and wash aqueous with ethyl acetate. Combine organic layers, dry (magnesium sulfate), and concentrate in vacuo to afford 90% (MW 242.11, 6.01 g) of 3.

EXAMPLE 4a

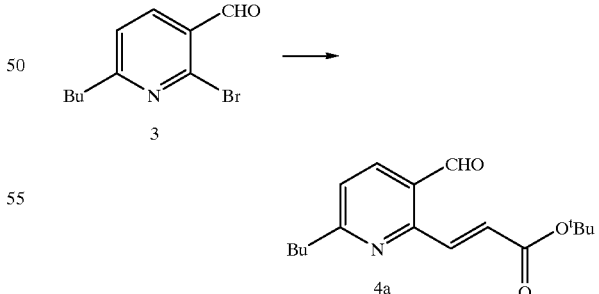

Preparation of 4a

Dissolve 3 (MW 242.11, 24.8 mmol, 6.01 g) in 75 mL toluene. Add sodium acetate (MW 82, 3 equ, 6.13 g), t-butyl acrylate (MW 128.17, d 0.875, 2.5 equ, 9.08 mL), P(o-tolyl)$_3$ (MW 304.38, 10 mol %, 755 mg) and allyl palladium chloride dimer (MW 365.85, 5 mol %, 455 mg). Age at reflux for 24 h. Cool, filter and evaporate in vacuo. Isolate

EXAMPLE 4b

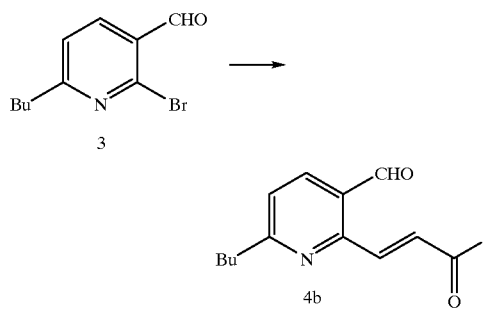

Preparation of 4b

Dissolve 3 (MW 242.11, 24.8 mmol, 6.01 g) in 75 mL toluene. Add sodium acetate (MW 82, 3 equ, 6.13 g), dimethylacrylamide (MW 99.13, d 0.962, 1 equ, 2.55 mL), $PPh_3$ (MW 262.29, 10 mol %, 653 mg) and allyl palladium chloride dimer (MW 365.85, 5 mol %, 455 mg). Age at 140° C. in sealed tube for 24 h. Cool, filter and evaporate in vacuo. Isolate 4b (MW 260.34) by silica gel chromatography (80:20 hexanes:ethyl acetate) in 70% yield (4.52 g).

4a (MW 289.37) by silica gel chromatography (92:8 hexanes:ethyl acetate) in 80% yield (5.74 g).

EXAMPLE 5a

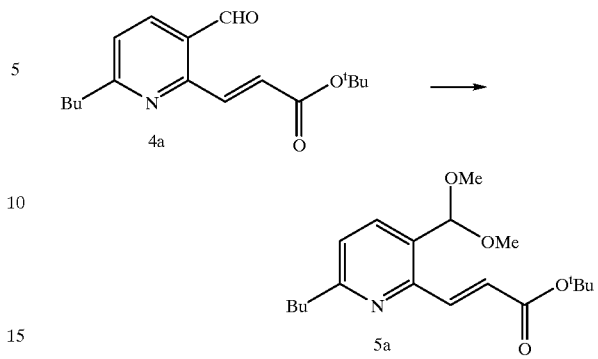

Preparation of 5a

A solution of 16.0 g (55.36 mmol) of aldehyde 4a and 1.4 g (5.54 mmol) of PPTS in 280 mL of MeOH was heated at reflux for 2.5 h. After cooling to room temperature, the solvents were evaporated in vacuo. The residue was dissolved into EtOAc and washed with satd. sodium bicarbonate solution. Concentration of the organic layer gave 18.2 g of the desired product 5a. 98% yield.

$^1$H NMR ($CDCL_3$) δ: 7.95 (d, 1H), 7.80 (d, 1H), 7.12 (d, 1H), 7.04 (d, 1H), 5.09 (1H), 3.45 (s, 6H), 2.80 (t, 2H),1.73 (m, 2H), 1.54 (s, 9 H), 1.40 (m, 2H), 0.95 (t, 3H) ppm.

EXAMPLE 6

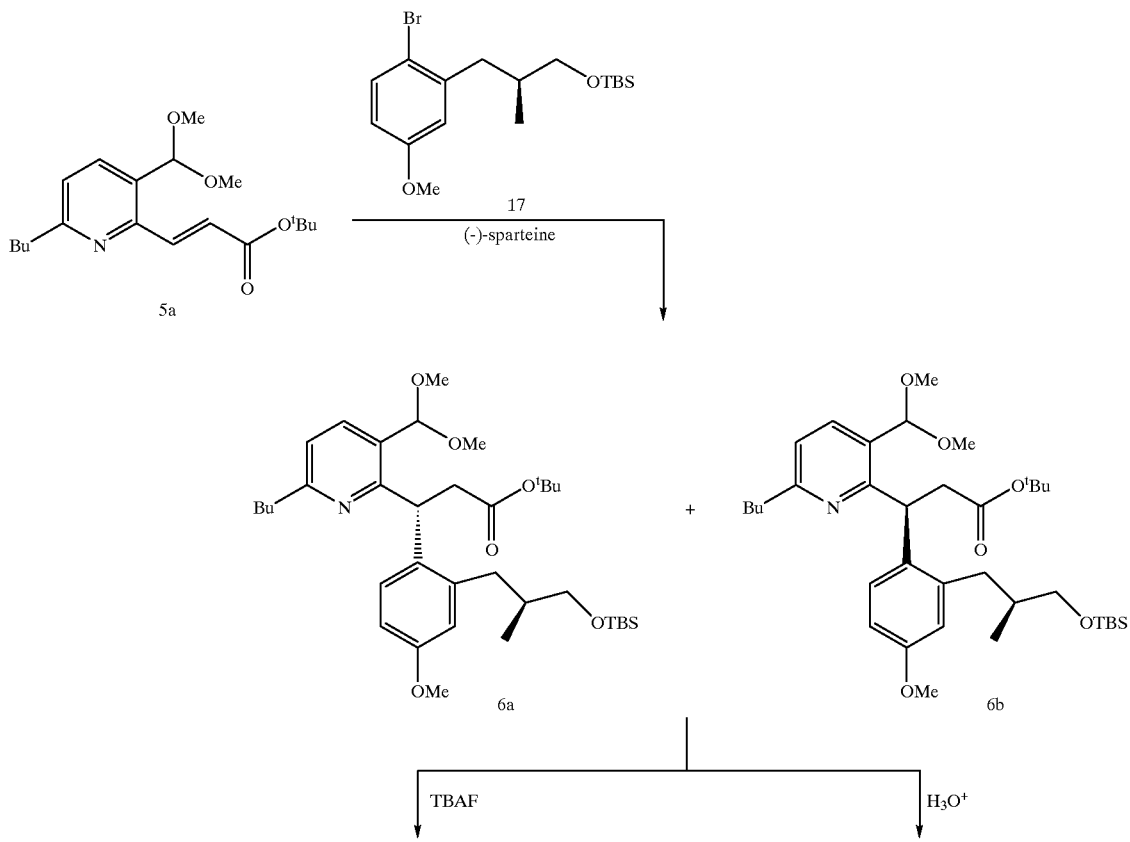

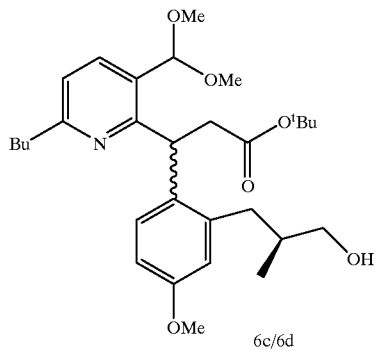

6c/6d

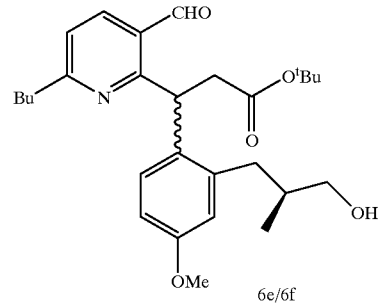

6e/6f

Step A: Preparation of 6a and 6b

To a solution of 17 (2.23 g, 5.97 mmol), (−)-sparteine (1.37 mL, 5.97 mmol), and THF (73 µL, 0.896 mmol) in 20 mL of toluene at −78° C. was added t-BuLi (1.7 M in Hexane, 7.0 mL, 11.94 mmol) dropwise. The solution was aged for 30 min. at −78° C. A solution of the unsaturated t-butyl ester 5a (1.0 g, 2.98 mmol) in 5 mL of toluene was added dropwise over 10 min. at −78° C. After 20 min at −78° C., the reaction was quenched with water. The organic phase was separated and dried over anhydrous sodium sulfate. Purification of the crude product by silica gel chromatography (EtOAc/Hex, 2:98) gave 1.52 g of the desired products 6a and 6b. 81% yield.

For major diasteromer 6b: $^1$H NMR (CDCL$_3$) δ: 7.24 (dd, 1H), 7.00 (d, 1H), 6.84 (d, 1H), 6.70 (d, 1H), 6.55 (dd, 1H), 5.74 (s, 1H), 5.02 (m, 1H), 3.72 (s, 3H), 3.55 (m, 4H), 3.22 (s, 3H), 2.92 (s, 3H), 2.80 (t, 2H), 2.50 (m, 2H), 2.12 (m, 1H), 1.75 (m, 2H), 1.40 (m, 2H), 1.28 (s, 9H), 0.95 (m, 6H), 0.90 (s, 9H), 0.09 (s, 3H), 0.08 (s, 3H) ppm.

In order to determine the ratio of the two diasteroisomers 6a and 6b, the above compounds were further deprotected by treatment with TBAF in THF or with either HCl or pTSA in aqueous acetone.

Step B: Preparation of 6c and 6d (Method A)

A solution of 500 mg (0.8 mmol) of above products 6a and 6b and 0.96 mL of TBAF (1.0 M in THF) in 6 mL of THF was allowed to stir for 4 h. at room temperature. The reaction solution was then washed with water and dried over sodium sulfate. The product was analyzed by H$^1$ NMR. Integration of the singlet peaks at 5.42 ppm (major diasteromer) and 5.38 ppm (minor diasteromoer) was used to determine the ratio of the two diasteromers.

Step C: Preparation of 6e and 6f (Method B)

A solution of 100 mg (0.16 mmol) of above products 6a and 6b in 3 mL of acetone and 1 mL of 5% HCl or 45 mg pTSA in 3 mL of acetone and 1 mL of water was allowed to stir for 5 h. at room temperature. The solvents were evaporated in vacuo. The residue was dissolved in EtOAc and washed with 10% sodium carbonate. The product was concentrated and analyzed by H$^1$ NMR. Integration of the singlet peaks at 10.35 ppm (major diasteromer) and 10.20 ppm (minor diasteromoer) was used to determine the ratio of the two diasteromers.

EXAMPLE 7

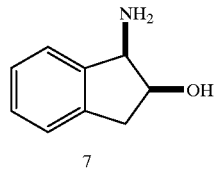

7

Preparation of 7

Compound 7 is a commericially available starting material, for example, see DSM Andeno, Grubbenvorsterweg 9, P.O. Box 81, 5900 AB Venlo, The Netherlands.

EXAMPLE 8

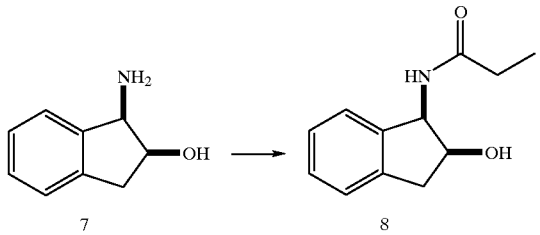

Preparation of 8

Na$_2$CO$_3$ (MW 105.99, 1.5 equ, 8.8 g) dissolved in 82 mL water. Add a solution of (1R,2S) amino indanol 7 (MW 149.19, 55.0 mmol, 8.2 g) in 160 mL CH$_2$Cl$_2$. Cool to −5° C. and add propionyl chloride (MW 92.53, d 1.065, 1.3 equ, 6.2 mL). Warm to 25° C. and age 1 h. Separate layers and dry organic (magnesium sulfate). Concentrate in vacuo to afford 8 (MW 205.26, 10 g) in 89% isolated yield.

EXAMPLE 9

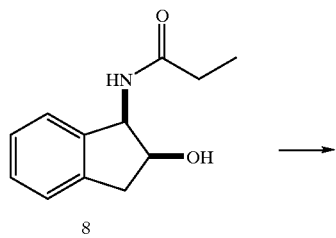

8

EXAMPLE 12

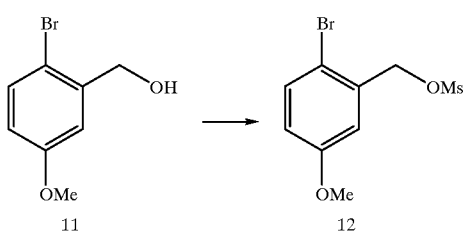

Preparation of 12

Dissolve 11 (MW 217.06, 47.2 mmol, 10.24 g) in 55 mL CH₂Cl₂ and cool to −20° C. Add DIEA (MW 129.25, d 0.742, 1.3 equ, 10.69 mL) then methane sulfonyl chloride (MsCl) (MW 114.55, d 1.480, 1.2 equ, 4.38 mL). Age −5° C. to 0° C. for 1 h then quench into 55 mL water. Extract with CH₂Cl₂ then wash with 1N H₂SO₄ (40 mL), then brine. Dry organic layers (magnesium sulfate) and concentrate in vacuo to afford 12 (MW 295.15, 13.23 g) in 95% yield.

EXAMPLE 13

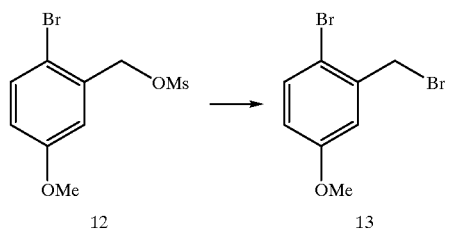

Preparation of 13

12 (MW 295.15, 44.8 mmol, 13.23 g) in 44 mL dimethylacetamide (DMAC). Add NaBr (MW 102.90, 2 equ, 9.22 g) and age 1 h. Add 88 mL water and collect solid by filtration. Wash cake with water and dry by suction. Quantitative yield of 13 (MW 279.96, 12.54 g) is obtained.

EXAMPLE 14

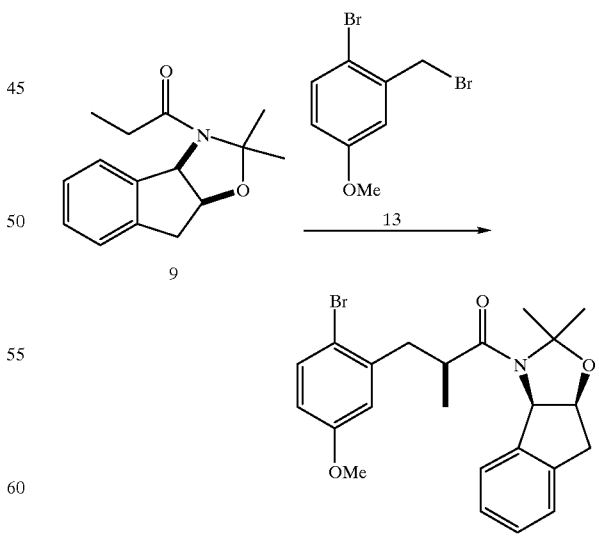

Preparation of 14

9 (MW 245.32, 1.1 equ, 89.1 g) in 1 L THF, cooled to −50° C. Add LiHMDS (1.0 M in THF, 1.5 equ, 545 mL) and

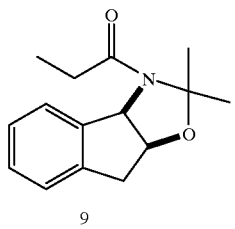

Preparation of 9

To a solution of 8 (MW 205.26, 49.3 mmol, 10 g) in 200 mL THF, add pyridinium p-toluenesulfonate (PPTS) (MW 251.31, 0.16 equ, 2 g) then methoxypropene (MW 72.11, d 0.753, 2.2 equ, 10.4 mL). Age 2 h at 38° C., then add aqueous sodium bicarbonate and ethyl acetate. The organic layer was dried (magnesium sulfate). After concentration in vacuo, 9 (MW 245.32, 12.09 g) was formed in quantitative yield.

EXAMPLE 10

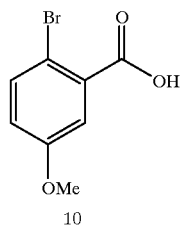

Preparation of 10

Compound 10 is a commericially available starting material, for example, see Lancaster Synthesis, P.O. Box 1000, Windham, N.H. 03087-9977 or Ryan Scientific, Inc., P.O. Box 845, Isle of Palms, S.C. 29451-0845.

EXAMPLE 11

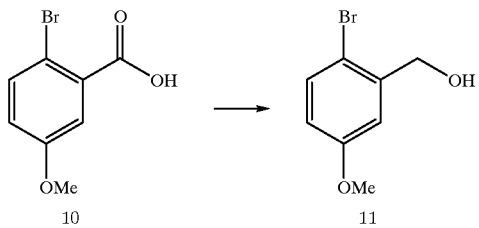

Preparation of 11

10 (MW 231.05, 130 mmol, 30.0 g) in 300 mL CH₂Cl₂ at 0° C. Add BH₃—SMe₂ (3 equ, 25.2 mL) and age for 2 h at 25° C. Quench into aqueous 2 N HCl and separate layers. Dry organic (magnesium sulfate) and concentrate in vacuo to obtain 94% yield of 11 (MW 217.06, 25.5 g).

age 1.5 h, warming to −30° C. Add 13 (MW 279.96, 327 mmol, 91.3 g) in 300 mL THF, and age −35° C. for 1 h. Warm to −10° C. over 1 h, then quench into aqueous NH₄Cl. Separate layers and extract with ethyl acetate. Dry organic and concentrate in vacuo to afford crude 14 (MW 444.37).

EXAMPLE 15

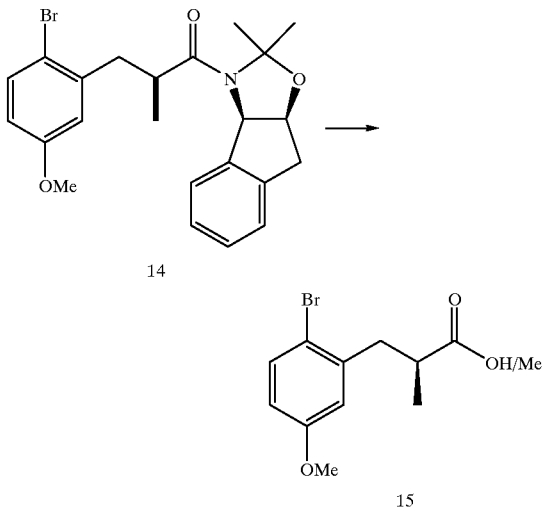

Preparation of 15

14 in 1 L MeOH and cooled to 10° C. Bubble in HCl gas for 1 h until reaction is complete. 2 L H₂O added and the product was filtered. The cake was washed with H₂O and dried to give the product hydroxyamide, which was then dissolved in 1 L MeOH and 1.5 L 6N HCl and refluxed overnight. The mixture was cooled to 25° C. and extracted with CH₂Cl₂ to give, after concentration, compounds 15 (60 g, 64% from bromide 13).

EXAMPLE 16

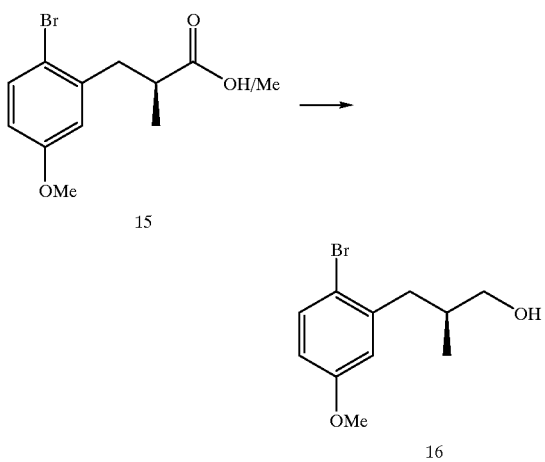

Preparation of 16

15 (mixture of acid and ester, 26.88 mmol) in 150 mL THF at −78° C. Add lithium aluminum hydride (LiAlH₄) (1 M in THF, 2 equ, 53.76 mL) over 30 min. Warm to 25° C. over 1 h, then quench into aqueous NH₄Cl. Add ethyl acetate, extract ethyl acetate. Wash organics with brine, dry (magnesium sulfate), and concentrate in vacuo to afford 95% yield of 16 (MW 259.14, 6.62 g).

EXAMPLE 17

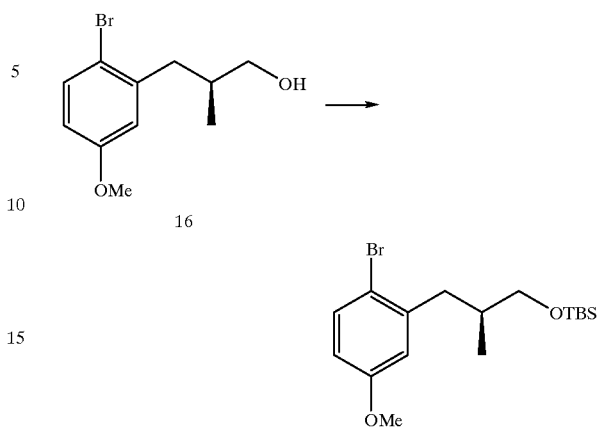

Preparation of 17

16 (MW 259.14, 25.54 mmol, 6.62 g) in 35 mL CH₂Cl₂ and cool to 0° C. Add imidazole (MW 68.08, 2.5 equ, 4.35 g) and then tert-butyldimethylsilyl chloride (TBSCl) (MW 150.73, 1 equ, 3.85 g). Age 1 h at 25° C. then quench with aqueous NaHCO₃ and add ethyl acetate. Extract with ethyl acetate, then dry organic layer (magnesium sulfate) and concentrate in vacuo to afford a quantitative yield of 17 (MW 373.41, 9.54 g).

$^1$H NMR (CDCl₃): 7.41 (d, J=8.74, 1H), 6.77 (d, J=3.04, 1H), 6.63 (dd, J=8.73, 3.06, 1H), 3.78 (s, 3H), 3.50 (d, J=5.75, 2H), 2.89 (dd, J=13.31, 6.15, 1H), 2.45 (dd, J=13.30, 8.26, 1H), 2.03 (m, 1H), 0.94 (s, 9H), 0.92 (d, J=5.01, 3H), 0.07 (s, 6H).

$^{13}$C NMR (CDCl₃): 159.1, 141.6, 133.2, 117.0, 115.4, 113.2, 67.4, 55.4, 39.7, 36.3, 26.0 (3C), 18.4, 16.5, −5.3 (2C).

EXAMPLE 18–22

Following the procedure described in Example 6 the listed chiral additive resulted in the indicated diastereomeric ratios of compounds 6a to 6b.

| Example No. | Chiral Additive | Diastereomeric Ratio (6a:6b) |
| --- | --- | --- |
| 6 | (−)sparteine | 1:5 |
| 18 | N-methyl ephedrine | 1:1 |
| 19 | Ph⟋⟍Me / MeO⟋⟍NMe₂ | 2.7:1 |
| 20 | Ph⟋⟍Ph / MeO⟋⟍OMe | 1:1.3 |

-continued

| Example No. | Chiral Additive | Diastereomeric Ratio (6a:6b) |
|---|---|---|
| 21 | 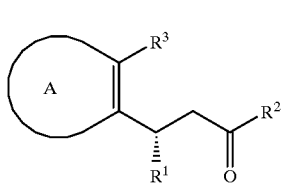 | 3.7:1 |
| 22 | 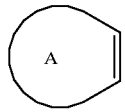 | 2.2:1 |

What is claimed is:

1. A process for the preparation of a compound of formula I:

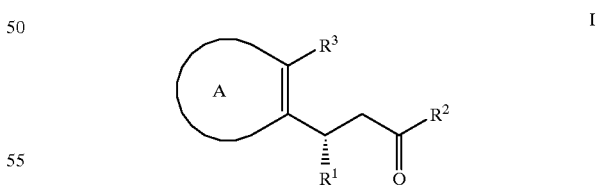

wherein

A represents:

a) 5- or 6-membered heterocyclyl containing one, two or three double bonds, but at least one double bond and 1, 2 or 3 heteroatoms selected from O, N and S, the heterocyclyl is unsubstituted or substituted with one, two or three substituents selected from the group consisting of: $CO_2R^4$, Br, Cl, F, I, $CF_3$, $N(R^5)_2$, $C_1-C_8$ alkoxy, $C_1-C_8$ alkyl, $C_2-C_8$ alkenyl, $C_2-C_8$ alkynyl, and $C_3-C_8$ cycloalkyl, b) 5- or 6-membered carbocyclyl containing one or two double bonds, but at least one double bond, the carbocyclyl is unsubstituted or substituted with one, two or three substituents selected from the group consisting of: $CO_2R^4$, Br, Cl, F, I, $CF_3$, $N(R^5)_2$, $C_1-C_8$ alkoxy, $C_1-C_8$ alkyl, $C_2-C_8$ alkenyl, $C_2-C_8$ alkynyl, and $C_3-C_8$ cycloalkyl, c) aryl, wherein aryl is as defined below, $C_1-C_8$ alkoxy, $C_1-C_8$ alkyl, $C_2-C_8$ alkenyl, $C_2-C_8$ alkynyl, or $C_3-C_8$ cycloalkyl, are unsubstituted or substituted with one, two or three substituents selected from the group consisting of: $CO_2R^4$, Br, Cl, F, I, $CF_3$, $N(R^5)_2$, $C_1-C_8$ alkoxy, and $C_3-C_8$ cycloalkyl, aryl is defined as phenyl or naphthyl, which is unsubstituted or substituted with one, two or three substituents selected from the group consisting of: $CO_2R^4$, Br, Cl, F, I, $CF_3$, $N(R^5)_2$, $C_1-C_8$ alkoxy, $C_1-C_8$ alkyl, $C_2-C_8$ alkenyl, $C_2-C_8$ alkynyl, and $C_3m-C_8$ cycloalkyl, and when two substituents are located on adjacent carbons they can join to form a 5- or 6-membered ring with one, two or three heteroatoms selected from O, N, and S, which is unsubstituted or substituted with one, two or three substituents selected from the group consisting of: H, $CO_2R^6$, Br, Cl, F, I, $CF_3$, $N(R^7)_2$, $C_1-C_8$ alkoxy, $C_1-C_8$ alkyl, $C_2-C_8$ alkenyl, $C_2-C_8$ alkynyl, and $C_3-C_8$ cycloalkyl, $R^1$ is:

a) $C_1-C_8$ alkyl, $C_2-C_8$ alkenyl, $C_2-C_8$ alkynyl, $C_3-C_8$ cycloalkyl, b) aryl, or c) heteroaryl;

heteroaryl is defined as a 5- or 6-membered aromatic ring containing 1, 2 or 3 heteroatoms selected from O, N and S, which is unsubstituted or substituted with one, two or three substituents selected from the group consisting of: $CO_2R^4$, Br, Cl, F, I, $CF_3$, $N(R^5)_2$, $C_1-C_8$ alkoxy, $C_1-C_8$ alkyl, $C_2-C_8$ alkenyl, $C_2-C_8$ alkynyl, and $C_3-C_8$ cycloalkyl, $R^2$ is $OR^4$ or $N(R^5)_2$;

$R^3$ is a) H, b) $C_1-C_8$ alkyl, c) $C_1-C_8$ alkenyl, d) $C_1-C_8$ alkynyl, e) $C_1-C_8$ alkoxyl, f) $C_3-C_7$ cycloalkyl, g) Br, Cl, F, I, h) aryl, i) heteroaryl, j) $N(R^5)_2$, or k) protected aldehyde;

n is: 0 to 5;

$R^4$ is $C_1-C_8$ alkyl;

$R^5$ is: $C_1-C_8$ alkyl, or aryl; and $R^6$ is: H, $C_1-C_8$ alkyl, and aryl; and $R^7$ are independently: H, $C_1-C_8$ alkyl, and aryl, when there are two $R^7$ substituents on a nitrogen they can join to form a 3- through 6-membered ring, which is unsubstituted or substituted with one, two or three substituents selected from the group consisting of: $CO_2R^4$, Br, Cl, F, I, $CF_3$, $N(R^5)_2$, $C_1-C_8$ alkoxy, $C_1-C_8$ alkyl, $C_2-C_8$ alkenyl, $C_2-C_8$ alkynyl, and $C_3-C_8$ cycloalkyl, comprising reacting an α,β-unsaturated ester or amide

I with an organolithium compound, $R^1Li$, in the presence of a chiral additive, which is a chiral compound different from the α,β-unsaturated ester or amide and organolithium compound, and an aprotic solvent at a temperature range of about −78° C. to about 0° C.

2. The process as recited in claim 1, wherein the number of equivalents of the organolithium compound, $R^1Li$, is 1 to about 4.

3. The process as recited in claim 2, wherein the chiral additive is selected from the group consisting of:

a) (−)-sparteine,
b) N,N,N',N'-tetra(C$_1$–C$_6$)-alkyltrans-1,2-diamino-cyclohexane, or
c)

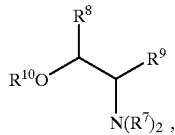

wherein R$^8$ and R$^9$ are independently: H, C$_1$–C$_6$ alkyl, C$_3$–C$_7$ cycloalkyl or aryl, except that R$^8$ and R$^9$ cannot simultaneously be H; and R$^{10}$ is H, C$_1$–C$_6$ alkyl or aryl.

4. The process as recited in claim 3, wherein the aprotic solvent is selected from the group consisting of tetrahydrofuran, diethyl ether, methyl t-butyl ether, benzene, toluene, hexane, pentane, and dioxane, or a mixture of said solvents.

5. The process as recited in claim 4, wherein the temperature range is about −78° C. to about −20° C.

6. A process for the preparation of a compound of formula I:

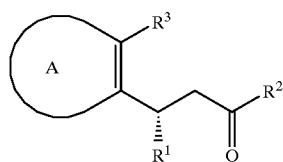

wherein

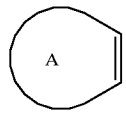

represents:
a) 5- or 6-membered heterocyclyl containing one, two or three double bonds, but at least one double bond and 1, 2 or 3 heteroatoms selected from O, N and S, the heterocyclyl is unsubstituted or substituted with one, two or three substituents selected from the group consisting of: CO$_2$R$^4$, Br, Cl, F, I, CF$_3$, N(R$^5$)$_2$, C$_1$–C$_8$ alkoxy, C$_1$–C$_8$ alkyl, C$_2$–C$_8$ alkenyl, C$_2$–C$_8$ alkynyl, and C$_3$–C$_8$ cycloalkyl,
b) 5- or 6-membered carbocyclyl containing one or two double bonds, but at least one double bond, the carbocyclyl is unsubstituted or substituted with one, two or three substituents selected from the group consisting of: CO$_2$R$^4$, Br, Cl, F, I, CF$_3$, N(R$^5$)$_2$, C$_1$–C$_8$ alkoxy, C$_1$–C$_8$ alkyl, C$_2$–C$_8$ alkenyl, C$_2$–C$_8$ alkynyl, and C$_3$–C$_8$ cycloalkyl,
c) aryl, wherein aryl is as defined below,
C$_1$–C$_8$ alkoxy, C$_1$–C$_8$ alkyl, C$_2$–C$_8$ alkenyl, C$_2$–C$_8$ alkynyl, or C$_3$–C$_8$ cycloalkyl, are unsubstituted or substituted with one, two or three substituents selected from the group consisting of: CO$_2$R$^4$, Br, Cl, F, I, CF$_3$, N(R$^5$)$_2$, C$_1$–C$_8$ alkoxy, and C$_3$–C$_8$ cycloalkyl,
aryl is defined as phenyl or naphthyl, which is unsubstituted or substituted with one, two or three substituents selected from the group consisting of: CO$_2$R$^4$, Br, Cl, F, I, CF$_3$, N(R$^5$)$_2$, C$_1$–C$_8$ alkoxy, C$_1$–C$_8$ alkyl, C$_2$–C$_8$ alkenyl, C$_2$–C$_8$ alkynyl, and C$_3$–C$_8$ cycloalkyl, and when two substituents are located on adjacent carbons they can join to form a 5- or 6-membered ring with one, two or three heteroatoms selected from O, N, and S, which is unsubstituted or substituted with one, two or three substituents selected from the group consisting of: H, CO$_2$R$^6$, Br, Cl, F, I, CF$_3$, N(R$^7$)$_2$, C$_1$–C$_8$ alkoxy, C$_1$–C$_8$ alkyl, C$_2$–C$_8$ alkenyl, C$_2$–C$_8$ alkynyl, and C$_3$–C$_8$ cycloalkyl, R$^1$ is:
a) C$_1$–C$_8$ alkyl, C$_2$–C$_8$ alkenyl, C$_2$–C$_8$ alkynyl, C$_3$–C$_8$ cycloalkyl,
b) aryl, or
c) heteroaryl;
heteroaryl is defined as a 5- or 6-membered aromatic ring containing 1, 2 or 3 heteroatoms selected from O, N and S, which is unsubstituted or substituted with one, two or three substituents selected from the group consisting of: CO$_2$R$^4$, Br, Cl, F, I, CF$_3$, N(R$^5$)$_2$, C$_1$–C$_8$ alkoxy, C$_1$–C$_8$ alkyl, C$_2$–C$_8$ alkenyl, C$_2$–C$_8$ alkynyl, and C$_3$–C$_8$ cycloalkyl, R$^2$ is OR$^4$ or N(R$^5$)$_2$;
R$^3$ is CHO,
n is: 0 to 5,
R$^4$ is C$_1$–C$_8$ alkyl;
R$^5$ is: C$_1$–C$_8$ alkyl, or aryl;
R$^6$ is: H, C$_1$–C$_8$ alkyl, and aryl;
R$^7$ are independently: H, C$_1$–C$_8$ alkyl, and aryl, when there are two R$^7$ substituents on a nitrogen they can join to form a 3- through 6-membered ring, which is unsubstituted or substituted with one, two or three substituents selected from the group consisting of: CO$_2$R$^4$, Br, Cl, F, I, CF$_3$, N(R$^5$)$_2$, C$_1$–C$_8$ alkoxy, C$_1$–C$_8$ alkyl, C$_2$–C$_8$ alkenyl, C$_2$–C$_8$ alkynyl, and C$_3$–C$_8$ cycloalkyl, comprising the steps of:

1) reacting an α,β-unsaturated ester or amide

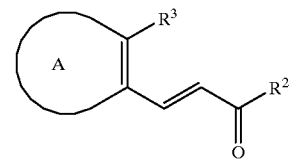

where R$_3$ is CH(OR$^4$)$_2$;
with an organolithium compound, R$^1$Li, in the presence of a chiral additive, which is a chiral compound different from the α,β-unsaturated ester or amide and organolithium compound and an aprotic solvent at a temperature range of about −78° C. to about 0° C. to give the conjugate adduct; and 2) removing the protecting group with an acid to give the compound of Formula I, where R$^3$ is CHO.

7. The process as recited in claim 6, wherein the number of equivalents of the organolithium compound, R$^1$Li, is 1 to about 4.

8. The process as recited in claim 7, wherein the chiral additive is selected from the group consisting of:
a) (−)-sparteine,
b) N,N,N',N'-tetra(C$_1$–C$_6$)-alkyltrans-1,2-diamino-cyclohexane, or
c)

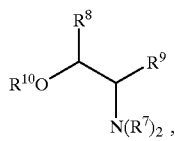

wherein $R^8$ and $R^9$ are independently: H, $C_1$–$C_6$ alkyl, $C_3$–$C_7$ cycloalkyl or aryl, except that $R_8$ and $R^9$ cannot simultaneously be H; and $R^{10}$ is H, $C_1$–$C_6$ alkyl or aryl.

9. The process as recited in claim 8, wherein the aprotic solvent is selected from the group consisting of tetrahydrofuran, diethyl ether, methyl t-butyl ether, benzene, toluene, hexane, pentane, and dioxane, or a mixture of said solvents.

10. The process as recited in claim 9, wherein the temperature range is about −78° C. to about −20° C.

11. A process for the preparation of

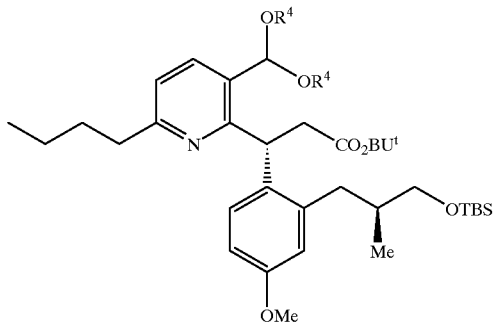

comprising reacting an α,β-unsaturated ester

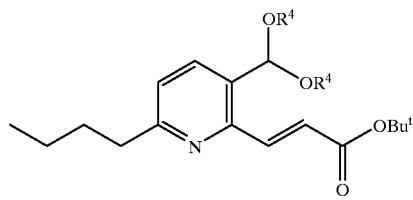

with an organolithium compound

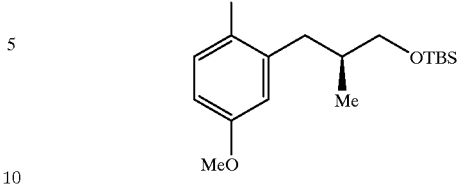

in the presence of a chiral additive, which is a chiral compound different from the α,β-unsaturated ester or amide and organolithium compound, and an aprotic solvent at a temperature range of about −78° C. to about −20° C.

12. The process as recited in claim 11, wherein the number of equivalents of the organolithium compound, $R^1Li$, is 1 to about 4.

13. The process as recited in claim 11, wherein the chiral additive is selected from the group consisting of:
   a) (−)-sparteine,
   b) N,N,N',N'-tetra($C_1$–$C_6$)-alkyltrans-1,2-diaminocyclohexane, or
   c)

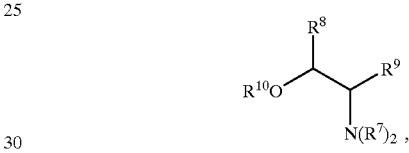

wherein $R^8$ and $R^9$ are independently: H, $C_1$–$C_6$ alkyl, $C_3$–$C_7$ cycloalkyl or aryl, except that $R^8$ and $R^9$ cannot simultaneously be H; and $R^{10}$ is $C_1$–$C_6$ alkyl or aryl.

14. The process as recited in claim 13, wherein the aprotic solvent is selected from the group consisting of tetrahydrofuran, diethyl ether, methyl t-butyl ether, benzene, toluene, pentane, hexane, and dioxane, or a mixture of said solvents.

15. The process as recited in claim 14, wherein the temperature range is about −78° C. to about −50° C.

16. The process as recited in claim 15, wherein the number of equivalents of the organolithium compound, $R^1Li$, is 1.5 to about 2.5.

17. The process as recited in claim 16, wherein the aprotic solvent is toluene or a toluene-hexane-(catalytic) tetrahydrofuran mixture.

18. The process as recited in claim 17, wherein the temperature range is about −78° C. to about −70° C.

* * * * *